United States Patent [19]

Vincent et al.

[11] 4,285,943

[45] Aug. 25, 1981

[54] NOVEL PHARMACEUTICAL COMPOSITIONS INCORPORATING AN ARYLTRIFLUOROETHANOL

[75] Inventors: Michel Vincent, Bagneux; Georges Remond, Versailles; Jacques Bure, Neuilly-sur-Seine, all of France

[73] Assignee: Science Union Et Cie, Suresnes, France

[21] Appl. No.: 90,636

[22] Filed: Nov. 2, 1979

[30] Foreign Application Priority Data

Nov. 3, 1978 [FR] France .................................. 78 31096

[51] Int. Cl.³ ...................... A61K 27/00; A61K 31/33; A61K 31/445; A61K 31/495

[52] U.S. Cl .................... 424/244; 424/248.5; 424/250; 424/267; 424/274; 544/158; 544/170

[58] Field of Search ........................ 424/248.5, 248.57; 544/158, 170

Primary Examiner—Stanley J. Friedman
Attorney, Agent, or Firm—Gordon W. Hueschen

[57] ABSTRACT

This invention relates to pharmaceutical compositions containing as active ingredient an aryltrifluoroethanol, and a process for producing the same.

These pharmaceutical compositions are useful for treating or alleviating pain, hyperpyretic conditions and/or inflammatory states.

9 Claims, No Drawings

NOVEL PHARMACEUTICAL COMPOSITIONS INCORPORATING AN ARYLTRIFLUOROETHANOL

PRIOR ART

The active ingredients have been previously disclosed as intermediate compounds in the U.S. patent application Ser. No. 949,571 to the same assignee, now abandoned.

SUMMARY OF THE DISCLOSURE

This invention relates to pharmaceutical compositions which incorporate as active ingredient an aryltrifluoroethanol, the aryl ring of which bears a cyclic amino structure, in admixture or conjunction with an inert pharmaceutical carrier or vehicle.

These pharmaceutical compositions may further include another active ingredient having a similar therapeutic activity or a synergistic activity.

This invention also relates to a method for treating or alleviating the painful conditions, the inflammatory states or the hyperpyretic conditions in the mammals.

This invention provides novel pharmaceutical compositions with analgetic, antipyretic and/or anti-inflammatory activity.

More precisely this invention relates to pharmaceutical compositions incorporating as active ingredient an aryltrifluoroethanol of the formula I:

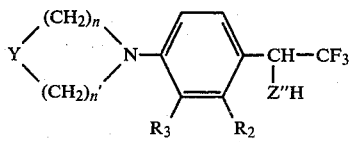

wherein
Y is a methylene grouping, a grouping

an oxygen or a carbon-carbon direct bond, in which
$R_4$ is a hydrogen or a lower alkyl radical
n and n', the same or different, are 2 or 3
Z'' is an oxygen or a sulphur atom
$R_2$ and $R_3$ are both hydrogen
in a racemic or optically-active form
in admixture or in conjunction with an inert non-toxic, pharmaceutically acceptable carrier or vehicle.

Moreover the pharmaceutical compositions according to this invention may also include a further active ingredient having a similar therapeutic activity or a synergistic activity.

Instead of a compound of formula I, an acid addition salt thereof may be used, namely a therapeutically-compatible acid addition salt.

The pharmaceutical compositions according to this invention are those intended or designed for the oral, parenteral or rectal routes of administration. However the percutaneous way, the permucous way or the sublingual way of administration may also be used.

Among the thus-defined pharmaceutical compositions, it may be particularly cited the tablets, the coated tablets, the dragees, the sachets, the pills, the capsules, the soft gelatine capsules, the syrups, the drinkable solutions or suspensions; the injectable suspensions or solutions packed in ampuls, multidoses flasks, autoinjectible syringes; suppositories.

For these pharmaceutical preparations the useful carriers or vehicles are namely the starches, cellulose, the chemically-modified celluloses, calcium carbonate, calcium phosphate, magnesium phosphate, silica, magnesium silicates, titanium silicates, talc, formolated case in for the dry preparations; water sugar syrups, isotonic salines for the liquid formulations; cocoa butter or polyethylenglycol stearates for the suppositories.

The useful dosology may broadly vary depending on the therapeutic use and the way of administration. The useful dosology may also vary depending on the weight and the age of the patient to be treated and the severity of the disease to be cured. Generally speaking, the dosology ranges from 0.050 to 0.600 g per unit dosage. For the pharmaceutical compositions intended for the parenteral or rectal routes of administration the amount of active ingredient of formula I or a salt thereof ranges from 0.100 to 0.500 g per unit dosage.

The daily dosology in the man ranges from 0.100 to 3 g administered once to four times per day.

As a compound of similar or synergistic activity it may be cited steroidal anti-inflammatory drugs such as cortisone, prednisone or betamethasone; an anti-inflammatory drug of the arylacetic or aryl propionic acid group such as indomethacin or profenid; sedatives such as barbiturates; a spasmolytic agent such a tiemonium iodide; an anti-infectious agent such as chloroquin or amodiaquin, an antibacterial agent such as penicillin.

The pharmaceutical compositions according to this invention posses valuable pharmacological properties. More precisely they show anti-inflammatory, and/or analgetic and/or antipyretic properties.

The anti-inflammatory effect is evidenced in the animals, namely in the rats with the CARRAGHENIN Test. The analgetic effect is evidenced using the writhing test caused by injection of phenylbenzoquinone, silver nitrate or acetic acid in the mice.

The antipyretic effect is evidenced using the hyperthermic test diclosed by J. J. LOUX and Cowrk. in Toxicology and Appl. Pharmacol. (1972) 22. 672.

Moreover the pharmaceutical compositions show only limited toxicity on the liver and on the kidneys. The acute toxicity thereof is reduced and the first occurances of death in the mice survene at elevated doses usually higher than 1.5 g/kg.

Therefrom the pharmaceutical compositions according to the invention are of value in human or veterinary medicine as analgetic, antipyretic or anti-inflammatory drug.

As analgetic drug they may be used for treating or alleviating pains from surgical origin such as in traumatology during or after surgical operation, alone or in combination with other analgetics or sedatives, pains from visceral origin, from bone diseases, from articular origin; cutaneomucous pains; in othorhinolaryngology, in gynaecology and pediatry.

As an antipyretic drug they found an use for treating any febrile condition from an infectious origin such as a viral disease, a parasitic disease, or correlated to an immunological response.

As an anti-inflammatory drug they found a use for improving the rheumatoic conditions such as arthritism or arthrosis as for example pelvispondylitis, scapulohumeral periarthritis or rheumatoid polyarthritis.

The pharmaceutical compositions are prepared according to the known methods of the pharmaceutical technology.

The following examples are merely intended to illustrate the invention. They do not limit it in any manner.

The starting material and the active ingredients are prepared according to the method disclosed in the Belgian patent No. 871 076 based on an application filed Oct. 6, 1978 and which Belgian patent was granted on Apr. 6, 1979, and which corresponds to U.S. Patent Application Ser. No. 949,571, filed Oct. 10, 1978.

EXAMPLE I

1-[(4-methylpiperazinyl)4-phenyl]2,2,2-trifluoro ethanol

Starting from 4-fluoro$\alpha\alpha\alpha$-trifluoroacetophenone and N-methyl piperazine the following compounds are successively obtained:

4(4-methylpiperazinyl-1)$\alpha\alpha\alpha$-trifluoroacetophenone MP=54°-55°

1[(4-methylpiperazinyl-1)phenyl]2,2,2-trifluoro ethanol MP=192°

Analysis $C_{13}H_{17}F_3N_2O=274.29$.

|  | C | H | N % |
|---|---|---|---|
| Calculated | 56.93 | 6.25 | 10.21 |
| Found | 57.04 | 6.36 | 10.20 |

EXAMPLE II

1-[(4-hexamethyleneimino)phenyl]2,2,2-trifluoroethanol

Using the procedure of example I the following compounds have been obtained:

1[(4-hexamethylene imino)2,2,2-trifluoro]acetophenone

1-[(4-hexamethylene imino)phenyl]2,2,2-trifluoroethanol melting at 71°-72°.

Analysis $C_{14}H_{18}F_3NO=273.3$.

|  | C | H | N % |
|---|---|---|---|
| Calculated | 61.53 | 6.64 | 5.12 |
| Found | 61.58 | 6.86 | 5.07 |

EXAMPLE III

1-[(4-heptamethylene imino)phenyl]2,2,2-trifluoroethanol

Using the same procedure as in example I they are successively obtained:

1-(4-heptamethylene imino)2,2,2-trifluoro acetophenone

1-[(4-heptamethylene imino)phenyl]2,2,2-trifluoroethanol melting at 77° C.

Analysis: $C_{15}H_{20}F_3NO=287.33$.

|  | C | H | N % |
|---|---|---|---|
| Calculated | 62.70 | 7.01 | 4.87 |
| Found | 63.80 | 7.30 | 4.89 |

This compound is slightly solvated

EXAMPLE IV

1-[(4-piperidinyl)phenyl]2,2,2-trifluoroethanol

Using the same procedure they are successively obtained:

1-(4 piperidinyl)2,2,2-trifluoroacetophenone

1-[(4-piperidinyl)phenyl]2,2,2-trifluoroethanol which melts at 100°-104°.

Analysis: $C_{13}H_{16}F_3NO=259.27$.

|  | C | H | N % |
|---|---|---|---|
| Calculated | 60.22 | 6.22 | 5.40 |
| Found | 60.38 | 6.00 | 5.49 |

This compound is soluble in the stoechiometric amount of N-aqueous solution of methane sulphonic acid.

By evaporating off the solvent, the corresponding methane sulphonate is recovered.

EXAMPLE V

Tablets containing 250 mg of 1-[4-(4-morpholino)phenyl]2,2,2-trifluoroethanol:

| | |
|---|---|
| 1-[4-(4-morpholino)phenyl]2,2,2-trifluoro ethanol | 2.500 Kg |
| Wheat starch | 0.650 kg |
| Mais starch | 0.450 kg |
| Carboxymethyl Cellulose | 0.100 kg |
| Ethyl Cellulose | 0.050 kg |
| Calcium Carbonate | 0.600 kg |
| Magnesium Carbonate | 0.050 kg |
| Kaolin | 0.210 kg |
| for 10.000 tablets weighing each about 450 mg | |

EXAMPLE VI

Drinkable suspension containing 200 mg of 1-[(4-hexamethylene imino)phenyl]2,2,2-trifluoroethanol per unit dosage

| | |
|---|---|
| active ingredient | 1.20 g |
| saccharose | 5 g |
| sorbitol | 2.50 g |
| methyl p.hydroxybenzoate | .095 g |
| propyl p.hydroxybenzoate | .025 g |
| flavor of fruits | .005 g |
| tragacanth gum | .45 g |
| water enough for | 100 ml | each tablespoon provides 200 mg of 1-[(4-hexamethylene imino)phenyl]2,2,2-trifluoroethanol.

EXAMPLE VII

Suppositories containing each 100 mg of 1-[(4-methyl piperazinyl)phenyl]2,2,2-trifluoroethanol

| | |
|---|---|
| active ingredient | 1 kg |
| yellow lack S | 0.65 g |
| polyethyleneglycol stearate | 11.500 kg |
| cocoa butter | 7.500 kg | for 10.000 suppositories each weighing about 2 g.

EXAMPLE VIII

Pharmacological study of the compounds of formula I (a) acute toxicity

The acute toxicity of the compounds of formula I has been determined on batches of 10 mices (swiss strain) which received orally the compound to be tested at increasing dosis. The mice are kept under survey for 8 days and the deaths, if any, are numbered.

The tested dosis ranged from 800 to 4000 mg/kg. In most of the cases, no mortality occurred with dosis lower than 1.5 g/kg. The average lethal dosis in the mice is about 2 g/kg.

(b) hepatic toxicity

The compounds of formula I and namely the most representative member of this group 4-(4-morpholino)-phenyl 2,2,2-trifluoroethanol have been administered once to rats or dogs previously fastened except for water, for 16 hours. The rats received either 500 or 1000 mg/kg of the compound to be tested. The dogs received 250 mg/kg of the compound to be tested orally suspended in a gum aqueous solution 24 and 48 hours after this ingestion the bloods are collected and the level of transaminases determined. Moreover in the rats an histologic control of the lever has been carried out.

Under similar conditions two lots of rats and a lot of dogs received paracetamol in order to show the level of hepatotoxicity.

The following results have been obtained.

Rats (Wistar strain) at 500 mg/kg.

| Product | Number of animals | SGPT after 24h in U/l | SGOT after 48h in U/l | Histology of the lever |
|---|---|---|---|---|
| Controls | 6 | 69 | 43 | nothing |
| Paracetamol | 6 | 162 | 67 | chromatolysis of the cells |
| compound of formula I | 6 | 52 | 51 | nothing |

Rat (Wistar strain) at 1000 mg/kg

| Product | Number of animals | SGPT after 24h in U/l | SGOT after 48h in U/l | Histology of the lever |
|---|---|---|---|---|
| Controls | 6 | 69 | 43 | nothing |
| Paracetamol | 6 | 1710 | 194 | chromatolysis picnosis |
| Compound of formula I | 6 | 87 | 94 | nothing abnormal |

Dogs at 250 mg/kg

| Product | Number of animals | SGPT after 24h in U/l | SGPT after 48h | SGOT after 24h | SGOT after 48h |
|---|---|---|---|---|---|
| Controls | 6 | 16 | 15 | 13 | 8 |
| Paracetamol | 6 | 80 | 61 | 13 | 7 |
| Compound Of formula I | 6 | 24 | 22 | 12 | 11 |

As it appears the hepato toxicity of the compounds of formula I is much lower than that of paracetamol and the histologic control of the hepatic cells does not show anything abnormal after ingestion of very high dosis of the compound of formula I.

(C) determination of the anti-inflammatory effect

The anti-inflammatory effect of the compounds of formula I has been evidenced using the Carraghenin test in the rat as disclosed by Winter.

Lots of 10 rats (Wishar strain) previously fastened are subcutaneously injected with a compound of formula I suspended or dissolved in an aqueous vehicle. 30 minutes after, the animals receive an injection of 1% solution of carrhaghenin in the plantar aponevrosis of the right paw. The volume of the paw is determined 3 hours after this injection in comparison with that of the non injected paw.

The compounds of formula I have been injected at dosis ranging from 20 to 320 mg/Kg. The average dosis which reduces from 50% the increase of the volume of the inflammated paw in comparison with the volume of the untreated paw is about 150 mg/kg.

(d) determination of the analgetic effect

The analgetic effect of the compounds of formula I has been determined according to the Phenylbenzoquinone Writhing Test in the mice as described by Hendershot (J Exp. Pharm. Therap. 125 (1959) 237).

Lots of 10 mice (Swiss Strain) received intraperitoneally an injection of 1 mg/kg phenylbenzoquinone. Prior to this injection the mice received by oral way in an aqueous vehicle a suspension or a solution of the compound of formula I at dosis ranging from 25 to 400 mg/kg.

The number of writhings are numbered for each mouse and an average value is calculated for each batch.

The average dosis which decreases of 50% the number of writhings in comparison of the average figure for the controls which received only the phenyl benzoquinone, range depending on the compound from 50 to 100 mg/kg.

Under similar conditions the average active dosis is 150 mg/kg for acetyl salicylic acid, 140 mg/kg for phenylbutazone and 100 mg/kg for diphenpyramide.

(e) determination of the antipyretic action

The antipyretic action of the compounds of formula I has been studied according to the technique disclosed by J. J. Loux and Cowork in Toxicology and Appl. Pharm. 22 (1972) 672. Accordingly a hyperthermic crisis appears after sub-cutaneous injection of baker's yeast.

The compounds to be tested are administered by oral way suspended in an aqueous vehicle 19 hours after the injection of the baker's yeast. The temperatures are measured and recorded through a thermistor 1 to 5 hours after the ingestion of the compound of formula I. The amount of active ingredient ingested ranged from 25 to 200 mg/kg. The variations of temperature of the rats were about 2° in the untreated animals. The animals treated with a compound of formula I shown only a moderate increase of the body temperature, namely 3 and 4 hours after the ingestion of the compound to be tested. The highest dosis (150 and 200 mg/kg) allowed a return to the initial temperature of the rats.

Under similar conditions batches of rats received an aqueous suspension of paracetamol at dosis ranging from 50 to 500 mg/kg. The average efficient dosis is substantially twice of that resulting from the treatment with a compound of formula I.

What we claim is:

1. A pharmaceutical composition incorporating as active ingredient an effective analgesic, antipyretic or anti-inflammatory amount of an aryltrifluoroethanol of the formula

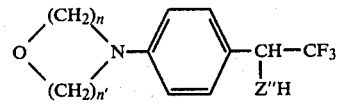

wherein
- n and n' are each 2; and
- Z" is oxygen; or a therapeutically compatible acid addition salt thereof; in admixture with a pharmaceutically-acceptable carrier or vehicle.

2. A composition according to claim 1 in dosage unit form useful for analgesic, antipyretic or antiflammatory purposes containing about 0.050 to about 0.600 g per dosage unit.

3. A pharmaceutical composition according to claim 1 wherein the active ingredient is in the racemic form or in an optically-active form.

4. A pharmaceutical composition according to claim 1 in which the active ingredient is in the form of an acid addition salt with a therapeutically-compatible mineral or organic acid.

5. A pharmaceutical composition according to claim 1 wherein the inert carrier or vehicle is that suitable for oral, parenteral or rectal administration.

6. A pharmaceutical composition according to claim 1 wherein the amount of active ingredient of formula I or a salt thereof ranges from 0.050 to 0.600 g per unit dosage.

7. A pharmaceutical composition according to claim 1 wherein the amount of active ingredient of formula I or a salt thereof ranges from 0.100 to 0.500 g for the formulation intended for the parenteral or rectal ways of administration.

8. A method for treating painful conditions from medical or surgical origin in a mammal suffering from pain which comprises administering to said mammal a safe but efficient amount to alleviate such condition, of a compound of claim 1.

9. The method of claim 8 wherein the safe but efficient amount of the claim 1 compound ranges from 0.050 to 0.600 g per unit dosage in said mammal.

* * * * *